US00PP16838P3

(12) United States Plant Patent
Khanizadeh

(10) Patent No.: US PP16,838 P3
(45) Date of Patent: Jul. 18, 2006

(54) STRAWBERRY PLANT NAMED 'SAINT-LAURENT D'ORLEANS'

(50) Latin Name: *Fragaria×ananassa dutch*
Varietal Denomination: Saint-Laurent d'Orleans

(75) Inventor: Shahrokh Khanizadeh, Baie D'Urfe (CA)

(73) Assignee: Her Majesty The Queen in Right of Canada, as represented by the Minister of Agriculture and Agri-Food Canada, St-Jean-sur-Richelieu (CA)

( * ) Notice: Subject to any disclaimer, the term of this patent is extended or adjusted under 35 U.S.C. 154(b) by 0 days.

(21) Appl. No.: 10/941,874

(22) Filed: Sep. 16, 2004

(65) Prior Publication Data

US 2006/0059591 P1 Mar. 16, 2006

(51) Int. Cl.
*A01H 5/00* (2006.01)

(52) U.S. Cl. ..... Plt./208
(58) Field of Classification Search ..... Plt./208
See application file for complete search history.

(56) References Cited

PUBLICATIONS

Baldwin, E. A. et al., Critical Reviews in Food Science and Nutrition, 1995, 35 (6), pp 509–524.
Gao, X. et al., J. Agric. Food Chem., 2000, 48, pp 1485–1490.
Kalt, W. et al., J. Agric. Food Chem., 1999, 47, pp 4638–4644.
Khanizadeh, S. et al., HortScience, 1999, 34 (4), pp 743–744.
Mayr, U. et al., J. Phytopathology, 1997, 145, pp 69–75.
Slinkard, K. et al., Am. J. Enol. Viticult., 1977, 28 (1), pp. 49–55.
Tsao, R. et al., J. Agric. Food Chem., 2003, 51, pp 6445–6451.
Tsao, R. et al., J. of Chromatography A., 2003, 1018, pp 29–40.
Wang, S.Y. et al., J. Small Fruit and Viticulture, 1994, 2 (4), pp 39–49.

*Primary Examiner*—Kent Bell
*Assistant Examiner*—Annette H Para
(74) *Attorney, Agent, or Firm*—Goudreau Gage Dubuc; Julie Gauvreau

(57) ABSTRACT

A new and distinct June-bearing strawberry cultivar named 'Saint-Laurent d'Orléans' is primarily adapted to the growing conditions of Eastern Central Canada and shows resistance to leaf diseases. Its high yields of very large, firm, light-red colored fruits, its long shelf life and high levels and activity of antioxidants essentially characterize 'Saint-Laurent d'Orléans'.

4 Drawing Sheets

Genus/species designation: *Fragaria×ananassa.*
Varietal denomination: 'Saint-Laurent d'Orleans'.

FIELD OF THE INVENTION

The present invention relates to a new and distinct June bearing strawberry cultivar designated as 'Saint-Laurent d'Orléans'. This cultivar belongs to the genus *Fragaria* (*×ananassa* Dutch.), whose fruits are juicy, edible and usually red, and are cultivated for culinary purposes.

BACKGROUND OF THE INVENTION

The new cultivar, tested as FIO9624-11, is the progeny of a cross made by Shahrokh Khanizadeh between 'L'Acadie'[1] and the selection SJ8916-1×Pink Panda. 'L'Acadie' is a June bearing strawberry cultivar (*Fragaria×ananassa* Dutch.) bred for Eastern Central Canada and more specifically for Quebec growing conditions. 'L'Acadie' is noted for large, firm fruits, moderate resistance to leaf diseases, partial resistance to red stele (*Phytophthora fragariae Hickman*), and keeping quality of several days after picking or maturity in the field. The selection SJ8916-1×Pink Panda has been used as parent for several years due to its hardiness, fruit quality and disease resistance in non replicated trails.

The cross took place in 1996 at the Horticultural Research and Development Center of the Agriculture and Agrifood Canada Research Station in St-Jean-sur-Richelieu, Québec. The 'Saint-Laurent d'Orléans' strawberry was asexually propagated by runners at the Agriculture and Agri-Food Canada sub-station in L'Acadie, Québec and extensively tested at the same location, where it has been tested since 1997. It was further tested in semi-commercial sites by Les Fraises de L'île d'Orléans Inc. in Saint Laurent, Île d'Orléans, Québec, Canada and by private partners, Meiosis Ltd in Kent, UK. 'Saint-Laurent d'Qrléans' is now an established and stable cultivar.

BRIEF SUMMARY OF THE INVENTION

'Saint-Laurent d'Orléans' is recommended for Eastern Central Canada, especially in areas where the climate is similar to that in the strawberry production areas of Quebec, such as i'Île d'Orléans. Typically, strawberry production in Quebec occurs in areas with winter temperatures down to −30° C. and warm and humid summers with unpredictable mixture of sun and rain (drought some seasons, constant rain other seasons). The very large, firm, light-red colored fruits, total yield in commercial fields, high antioxidant activity and the leaf disease resistance essentially characterize 'Saint-Laurent d'Orléans', as compared to the well-known variety 'Kent' for example. The fruits of 'Saint-Laurent d'Orléans' are ideal for pick your own, fresh market and shipping.

BRIEF DESCRIPTION OF THE DRAWINGS

The accompanying color photographs show typical specimens of the new variety at various stages of development as nearly true as it is possible to make in color reproductions.

DETAILED BOTANICAL DESCRIPTION

Figure 1:
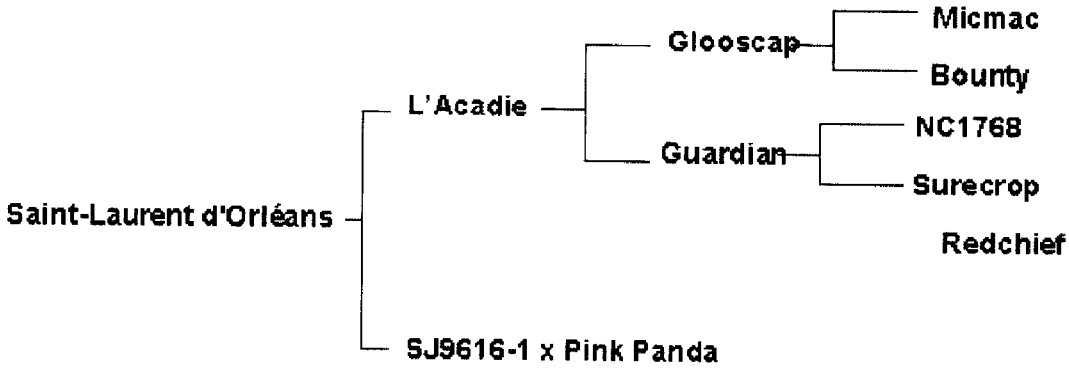
FIG. 1 shows a schematic pedigree of 'Saint-Laurent d'Orléans'.

'Saint-Laurent d'Orléans' is a June bearing strawberry cultivar (*Fragaria×ananassa* Duch.) with an early flowering date and mid-season harvest maturity. It is a progeny (FIO9624-11) resulting from a cross between two recent released from the Horticulture Research and Development Center (HRDC) of Agriculture and Agri-Food Canada, 'L'Acadie' and the selection 'SJ8916-1×Pink Panda'. 'Saint-Laurent d'Orléans' has high yields of very large, firm, light-red colored fruits and performs a much longer storage life than the standard variety 'Kent', used by many growers. It also shows higher levels of antioxidant activity than 'Kent', which makes it ideal for growers who need to store the fruits for several days or ship them to other provinces for marketing.

The selection was named after the village of St-Laurent d'Orléans, which is located at the south of l'Île d'Orléans, Quebec. In this area the principal economy comes from agriculture, with a major emphasis on vegetable and strawberry production. This village is known as a capital of strawberry production in Quebec and is recognized for high quality fruits production.

Plants of 'Saint-Laurent d'Orléans' are of medium vigor, have a flat globose growing habit and produce 4 to 5 inflorescences per crown. They can tolerate winter air temperatures down to −30° C. with 10 cm straw mulch cover, and perform very well in both heavy fine textured, course textured and light soil conditions.

Plant Characteristics

Plant:

*Habit.*—Globose.

*Density (of individual plants in hill culture or plants/m 2 for matted rows).*—Medium to dense.

*Number of crowns per plant.*—Average 2.

*Vigor.*—Medium to strong.

*Low temperature tolerance.*—High.

Stolon Characteristics

Stolon:

*Number.*—Medium.

*Thickness.*—Average 2.4 mm.

Fruit Characteristics

'Saint-Laurent d'Orléans' fruits, fruit production and fruit quality characteristics.

TABLE 1

Cumulative yield (g.m$^{-1}$ of row), fruit weight, firmness, flavour, skin color, shelf life at room temperature and ripening season of 'Saint-Laurent d'Orléans' as compared to 'Kent' and 'Yamaska' Averages of four replicates from 2002 harvest

| Genotypes | Total yield (g/m$^{-1}$)[x] | Wt./fruit (g)[x] | Firmness[y] | Flavor[y] | Skin color[y] | Shelf life at 20° C.[x] | Ripening season[w] |
|---|---|---|---|---|---|---|---|
| Saint-Laurent d'Orléans | 14553.8 | 11.3 | 4.0 | 4.0 | 2.7 | 5.0 | LM |
| Yamaska | 5871.1 | 10.6 | 3.6 | 3.5 | 3.6 | 5.0 | L |
| Kent | 8403.6 | 8.2 | 2.8 | 4.0 | 3.4 | 1.5 | EM |
| Prob ≦ 0.05 | ** | * | * | Ns | * | * | — |

[x]Data taken from a 1-meter long representative portion of a 2-meter matted row (width 50 cm).
[y]Data were transformed to arcsin prior to analysis of variance (SAS institute, 1988)[2].
Firmness: 1 = very soft, 5 = very firm
Flavor: 1 = poor, 5 = excellent
Skin color: 1 = very pale, 5 = dark red
[x]Number of days at room temperature (20° C.) for which the fruits were more than 95% marketable.
[w]L =Late, LM = Late–Midseason, M = Midseason, EM = Early–Midseason.
Significance: ** 0.01, * 0.05, Ns not significant

TABLE 2

Antioxidant capacity and total phenolic content of 'Saint-Laurent d'Orléans', as compared to 'Kent'[x] Data collected in L'Acadie site (Québec)

| | Total antioxidant capacity | | | | Content |
|---|---|---|---|---|---|
| | TEAC[a] (μmol.mg$^{-1}$) | | | FRAP[b] (μM) | Total phenols[c] (ppm) |
| Genotype | crude | aqueous | lipophilic | crude | crude |
| Saint-Laurent d'Orléans | 242.5 | 247.9 | 40.2 | 2478.4 | 139.4 |
| Kent | 198.8 | 228.6 | 29.6 | 2131.5 | 106.1 |
| Least Significant Difference (LSD) | 32.9 | 24.0 | 9.8 | 1191.1 | 77.5 |

[a]TEAC: Trolox Equivalent Antioxidant Capacity expressed as μmol Trolox equivalent mg$^{-1}$ dry weight
[b]FRAP: Ferric-Reducing Antioxidant expressed as μM FRAP
[c]Total phenols expressed as ppm gallic acid equivalent.

Fruit:

*Ratio of length/maximum width.*—Slightly longer than broad.

*Size.*—Average 10.0 to 14.9 g.

*Predominant shape.*—Round and globose conic.

*Difference in shape between primary and secondary fruits.*—None to very slight.

*Band without achenes.*—Medium.

*Unevenness of surface.*—Very weak to medium.

*Skin color.*—RHS 45A and 46A.

*Evenness of color.*—Slightly uneven.

*Glossiness.*—Strong.
*Insertion of achenes.*—Slightly below surface of fruit.
*Color of achenes.*—RHS 150C.
*Hollow center size.*—Absent.
*Insertion of calyx.*—Slightly set above fruit to level with fruit.
*Pose of the calyx segments.*—Flat.
*Size of the calyx in relation to fruit diameter.*—Slightly smaller to slightly larger.
*Adherence of the calyx.*—Strong.
*Firmness of flesh* (*when fully ripe*).—Firm.
*Color of flesh.*—RHS 46A to 187A.
*Evenness of color of flesh.*—Slightly uneven to slightly even.
*Sweetness.*—Medium.
*Acidity.*—Medium to medium strong.
*Time of flowering* (*50% of plants of first flower*).—Early.
*Harvest maturity* (*50% of plants with ripe fruits*).—Mid-season.
*Type of bearing.*—Not everbearing.

'Saint-Laurent d'Orléans' differs from its parents ('L'Acadie' and the selection 'SJ8916-1×Pink Panda') in terms of fruit shape, fruit quality and yield. 'Saint-Laurent d'Orléans' fruits are round and globose-conic with non-reflexed sepals, the tips of which sometimes touch the fruit. 'L'Acadie' fruits are conic with a white small neck under the semi-reflexed calyx and a glossier surface than 'Saint-Laurent d'Orléans'. The selection 'SJ8916-1×Pink Panda' has fruits that are firmer than those of 'Saint-Laurent d'Orléans' but a much lower yield.

Figure 2:
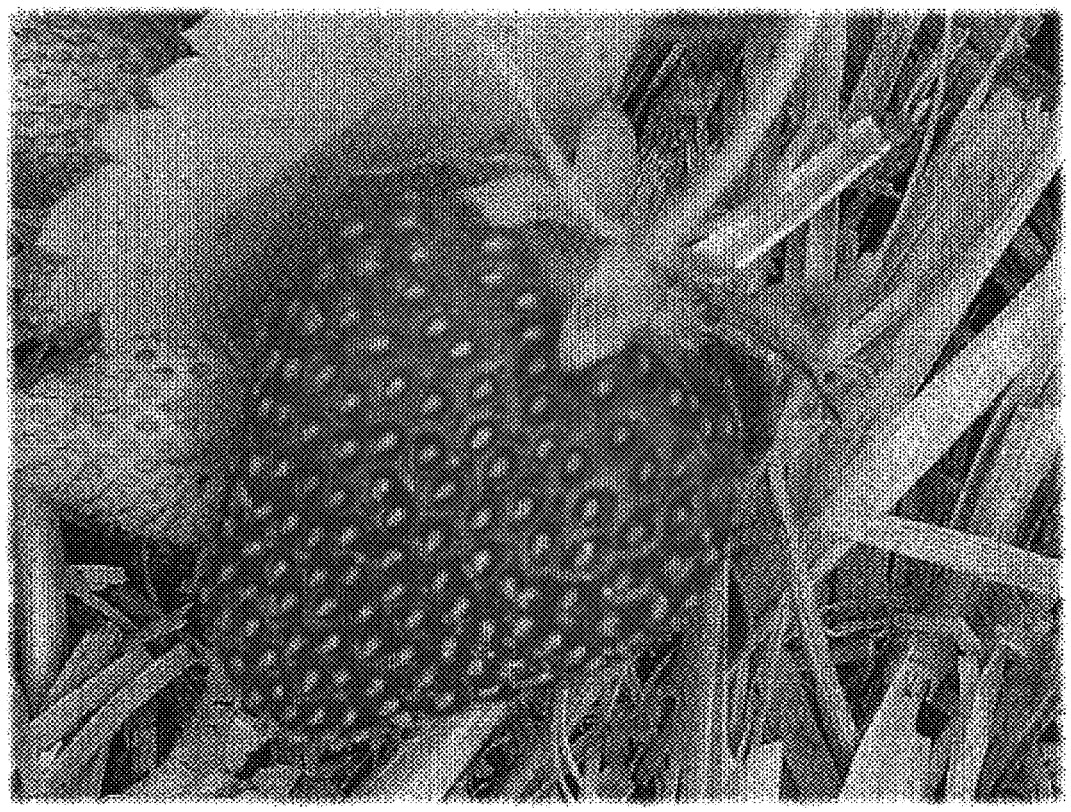
FIG. 2 shows a close-up view of a 'Saint-Laurent d'Orléans' fruit.
Figure 3:
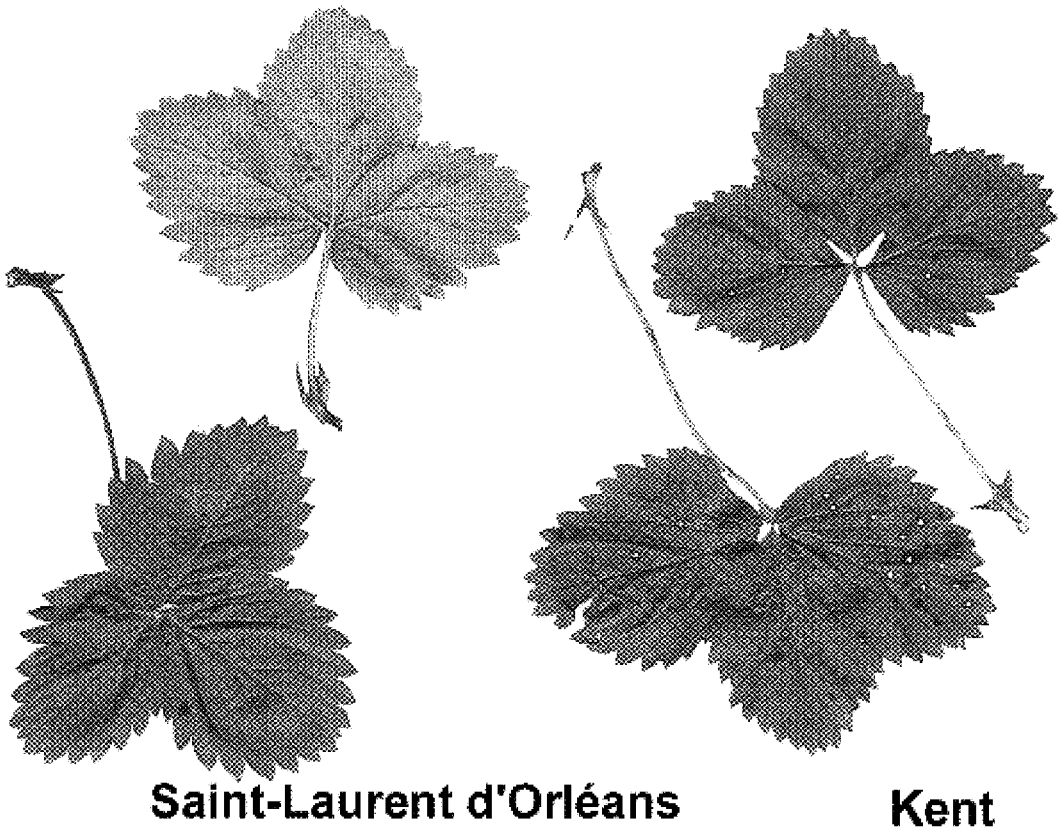
FIG. 3 shows a comparison of trifoliates between 'Saint-Laurent d'Orléans' and 'Kent'.
Figure 4:
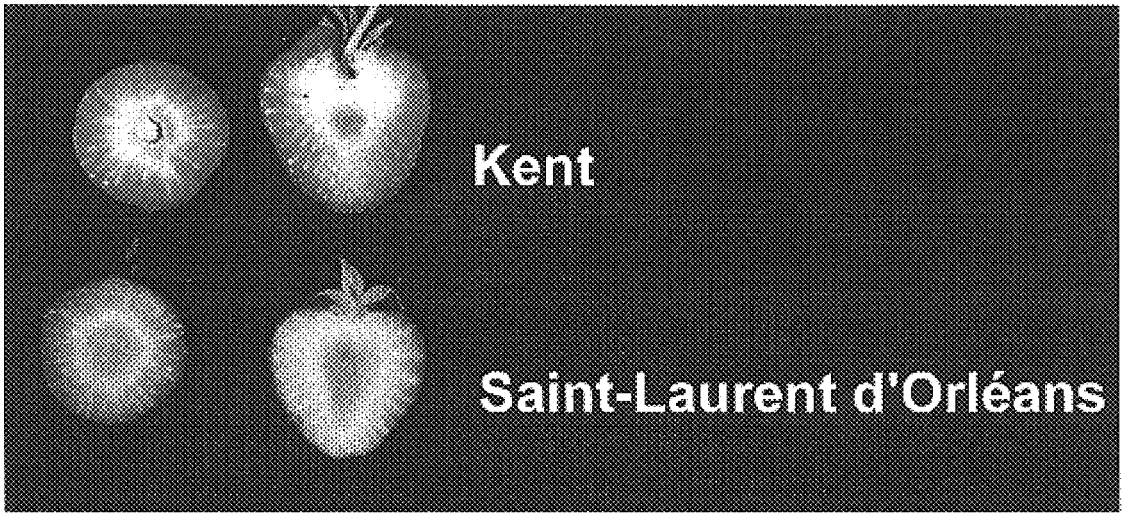
FIG. 4 shows a comparison of internal fruit characteristics between 'Saint-Laurent d'Orléans' and 'Kent'.

'Saint-Laurent d'Orléans' produces perfect white flowers, which when pollinated and ripen fully result in attractive and large red shiny fruits (FIG. 2). The flesh is medium to dark red (RHS 46A to 187A) almost throughout and firm. Fresh fruits store well for up to 4–5 days at room temperature and longer under refrigeration.

'Saint-Laurent d'Orléans' produces significantly higher yield and larger fruits size than 'Kent' (Table 1) in replicated trials at several locations. The fruits are also firmer, with lighter red skin color, and have longer shelf life at room temperature than 'Kent' (Table 1). 'Saint-Laurent d'Orléans' is a late mid-season cultivar with fifty percent of primary fruits ripe by early July in L'Acadie, Quebec.

Total antioxidant activity of the fruit of 'Saint-Laurent d'Orléans' measured by ABTS cation radical-scavenging assay[3] showed high TEAC (trolox equivalent antioxidant capacity) levels in the crude and aqueous extract (242.5 and 247.9 μmol/mg, respectively) while the lipophilic extract (40.2 μmol/mg) showed the lowest activity (Table 2). Thus, the antioxidant capacity recorded to 'Saint-Laurent d'Orléans' was higher than that of the 'Kent' cultivar (Table 2). However, the antioxidant capacity measured by ferric-reducing antioxidant power (FRAP), total phenolics and phenolic composition (benzoic acids, hydroxycinnamic acids, ellagic acids, flavonols and anthocyanins) performed according to Tsao et al.[4], Slinkard and Singleton[5] and by HPLC analysis[6] did not show significant differences between the two cultivars (Table 2), except for benzoic acids and anthocyanins, for which 'Saint-Laurent d'Orléans' showed lower levels than 'Kent' (6.4, 10.5 ppm gallic acid equivalent and 77.2, 103.8 ppm cyanidins-3-galactoside equivalent, respectively).

The potential of 'Saint-Laurent d'Orléans' (antioxidant content and high activity) could contribute to its quality preservation and disease resistance. Indeed, the phenolic compounds of various fruits have been widely shown to protect plant tissues against external stresses and participate to disease resistance[7,8,9]. These compounds may act as flavorants, colorants or antioxidants to extend shelf life and enhance quality preservation[10]. Moreover, release of new strawberry fruits with higher antioxidants capacity levels may be able to stimulate greater interest in the nutraceutical aspects to strawberry consumption and potentially help to reduce risks of cancers and heart diseases.

Foliage Characteristics

Leaf:
*Green color of upper side.*—RHS 137C or 138A.
*Green color of lower side.*—RHS 138C.
*Blistering* (*interveinal blisters*).—Very weak to medium weak.
*Number of leaflets.*—Three.

Terminal leaflet:
*Profile.*—Cupped.
*Length/width ratio.*—Slightly longer than broad.
*Shape of base.*—Obtuse.
*Shape of teeth.*—Acute to obtuse.

Petiole:
*Length.*—Average 17 cm.
*Pubescence.*—Medium to medium dense.
*Pose of hairs.*—Outwards.
*Color of top.*—RHS 138C.
*Color of bottom.*—RHS 185A.

Inflorescence, Fruiting Truss and Flower Characteristics

Inflorescence:
*Position relative to foliage.*—Below to level with.

Fruiting truss:
*Attitude of fruiting trusses* (*at first picking*).—Semi erect.
*Length of fruiting trusses.*—Average of 12 to 15 cm measured from the crown to the 1$^{st}$ split.

Flowers:
*Flower size.*—Average 2.6 cm for secondary flowers.
*Corolla size.*—Average 2.8 cm for secondary flowers.
*Calyx size.*—Average 2.8 cm.
*Color of opened flower.*—White.
*Diameter of calyx relative to corolla.*—Smaller to same size.
*Diameter of inner calyx relative to outer* (*on secondary flowers*).—Same size.
*Spacing of petals* (*secondary flowers with 5 to 6 petals*).—Free to touching.
*Size of petals.*—Average 0.9 cm.
*Petal length/width ratio* (*on secondary flowers*).—As long as broad to longer than broad.

'Saint-Laurent d'Orléans' demonstrates a higher degree of resistance to leaf diseases as compared to 'Kent'. 'Saint-Laurent d'Orléans' is moderately susceptible to leaf spot (*Mycosphaerella fragariae* (Tul.) Lindau) and resistant to moderately resistant to leaf scorch (*Diplocarpon earlina* Ell. & Ev.). 'Saint-Laurent d'Orléans' also ranked as low susceptibility to *verticillium* wilt (*Verticillium* albo-atrum Reinke & Berth.) as compared to 'Jewel' and 'Seascape' that ranked intermediate (data not shown).

Tests and Trials

Tests and trials for 'Saint-Laurent d'Orléans' were conducted in matted rows at the Agriculture & Agrifood Canada experimental farm in l'Acadie, Québec since 1997. A completely randomized design for four replicates (4 plots) was used to evaluate the selections. Each experimental unit was a 4-meter long plot, 50 cm wide. A representative 2 m section of the plot was used for data collection. The remainder was used as guard row.

References

1. Khanizadeh, S., B. Thériault, O. Carisse and D. Buszard, 1999. *AC-L'Acadie Strawberry.* HortScience 34(4): 743–744.
2. SAS Institute. 1988. *Statistical analysis system. SAS/STAT, SAS/BASIC guide for personal computers,* version 6.04 (ed.) SAS Inst. Cary, N.C.
3. Gao, X., M. Ohlander, N. Jeppsson, L. Bjork and V. Trajkovski, 2000. *Changes in antioxidants effects and their relationship to phytonutrients of Sea Buckthorn (Hippophae rhamnoides L) during maturation.* J. Agric. Food Chem. 48:1485–1490.
4. Tsao, R., R. Yang and J. C. Yang. 2003. *Antioxidant isoflavones in Osage Orange, Maclura pomifera (Raf.) Schneid.* J. Agric. Food Chem. 51: 6445–6451.
5. Slinkard, K. and V. L. Singleton. 1977. *Total phenol analysis: automation and comparison with manual methods.* Am. J. Enol. Viticult. 28:49–55.
6. Tsao, R. and R. Yang. 2003. *Optimization of a new mobile phase to known the complex and real Polyphenolic composition: towards a total phenolic index using high-performance liquid chromatography.* J. Chromatogr. A. 1018:29–40.
7. Wang, S. Y., J. L. Maas, J. A. Payne and G. Galleta. 1994, *Ellagic acid in small fruits, mayhaws, and other plants.* J. Small Fruit and Viticulture 2 (4): 39–49.
8. Mayr, U., Michalek, S., Treutter, D. and W. Feucht. 1997, *Phenolic compounds of apple and their relationship to scab resistance.* J. Phytopathology 145: 69–75.
9. Kalt, W., C. F. Forney, A. Martin, and R. L. Prior. 1999. *Antioxidant capacity, vitamin C, phenolics, and anthocyanins after fresh storage of small fruits.* J. Agric. Food Chem. 47: 4638–4644.
10. Baldwin E. A., M. O. Nisperos-Carriedo and R. A. Baker. 1995. *Use of edible coatings to preserve quality of lightly processed products.* Crit. Rev. Food Sci. Nutr. 35:509–24.

What is claimed is:

1. A new and distinct strawberry plant named 'Saint-Laurent d'Orléans' as described and illustrated herein.

* * * * *